United States Patent [19]
Li et al.

[11] Patent Number: 5,759,854
[45] Date of Patent: Jun. 2, 1998

[54] NEUROTRANSMITTER TRANSPORTER

[75] Inventors: Yi Li; Robert D. Fleischmann, both of Gaithersburg, Md.

[73] Assignee: Human Genome Sciences, Inc., Rockville, Md.

[21] Appl. No.: 424,424

[22] PCT Filed: May 16, 1994

[86] PCT No.: PCT/US94/05363

§ 371 Date: Apr. 21, 1995

§ 102(e) Date: Apr. 21, 1995

[87] PCT Pub. No.: WO95/31539

PCT Pub. Date: Nov. 23, 1995

[51] Int. Cl.$^6$ .................................................. C12N 15/12
[52] U.S. Cl. ..................... 435/325; 536/23.5; 435/320.1; 435/252.3
[58] Field of Search ........................ 435/6, 69.1, 240.2, 435/252.3, 320.1, 325; 536/23.5; 530/350; 514/2, 12

[56] References Cited

FOREIGN PATENT DOCUMENTS

| 9308261 | 4/1993 | WIPO | C12N 1/20 |
| 9310228 | 5/1993 | WIPO | C12N 15/00 |

OTHER PUBLICATIONS

Liu, Q.R. et al., Molecular Characterization of Four Pharmacologically Distinct Alpha-Aminobutyric Acid Transporters in Mouse Brain. J. Biol. Chem., 268:2106–2112 (1993).

Pantanowitz, S. et al., Only One of the Charged Amino Acids Located in the Transmembrane Alpha–Helices of the Gama Aminobutyric Acid Transporter (Subtype A) is Essential For Its Activity. J. Biol. Chem., 268:3222–3225 (1993).

Liu, Q.R. et al., A Rat Brain cDNA Encoding the Neurotransmitter Transporter With an Unusual Structure. FEBS, 315(2):114–118 (1993).

Mestikawy, S.E. et al., Characterization of an Atypical Member of the Na+/Cl− –Dependent Transporter Family: Chromosomal Localization and Distribution in GABAergic and Glutamatergic Neurons in the Rat Brain. Journal of Neurochem., 62:445–455 (1994).

Van Winkle, L.J., Endogenous Amino Acid Transport Systems and Expression of Mammalian Amino Acid Transport Proteins in Xenopus Oocytes. Biochemica Et Biophys. Acta, 1154:157–172 (1993).

Uhl, G.R. and Hartig, P.R., Transporter Explosion: Update on Uptake. Tips, 13:421–425 (1993).

Borden, L.A. et al., Molecular Heterogeneity of the Gamma–Aminobutyric Acid (GABA) Transport System, J.Biol.Chem., 267(69):21098–21104 (1992).

Uhl, G.R. et al., Neurotransmitter Transporter Family cDNAs In a Rat MidBrain Library: 'Orphan Transporters' Suggest Sizable Structural Variations. Mol. Brain Res., 16:353–359 (1992).

Clark, J.A. and Amara, S.G., Amino Acid Neurotransmitter Transporters Structure, Function, and Molecular Diversity. BioEssays, 15(5):323–332 (1993).

*Primary Examiner*—Marianne P. Allen
*Attorney, Agent, or Firm*—Elliot M. Olstein; J. G. Mullins

[57] ABSTRACT

Disclosed is a neurotransmitter transporter protein and DNA (RNA) encoding such protein. Also provided is a procedure for producing such polypeptide by recombinant techniques. The procedure for producing antagonists/inhibitors against such polypeptide is also provided. Such antagonists/inhibitors may be used to inhibit the action of neurotransmitter transporter protein for treatment of depression, anxiety of epilepsy.

14 Claims, 5 Drawing Sheets

FIG. 1A

```
         10                  30                  50
CGGAGGCAGGGAGTGAGGAGCGAGTCGCGGTGCCGCGGCGAGCTCCGGGTCGCC
         70                  90                 110
CCAGCCCCAGCCGGGGGCCTGTGCGGGAGGAGCTGTGCTCCGGACCCGTCGGGGA
        130                 150                 170
TCGCAGCTGCTCGGCCGAGTGCACGGGCCGAGTCTGCCGACTACCACGCTGACAGG
        190                 210                 230
TCCCTGAATGAGAAGGAGCTGACAGCAGCTGAATTCCATCTTCTCTGTGTGCTGGGAGC
        250                 270                 290
AGGGCTACACGGCCCAGGTGGCATCAATGCCGAAGAACAGCAAAGTGACCCAGCGTGAGC
            M   P   K   N   S   K   V   T   Q   R   E   H
        310                 330                 350
ACAGCAGTGAGCATGTCACTGAGTCCGTGGCCGACCTGCTGGCCCTCGAGGAGCCTGTGG
  S   S   E   H   V   T   E   S   V   A   D   L   L   A   L   E   E   P   V   D
        370                 390                 410
ACTATAAGCAGAGTGTACTGAATGTGGCTGGTGAGGCAGGCGGCAAGCAGAAGGCGGTGG
  Y   K   Q   S   V   L   N   V   A   G   E   A   G   G   K   Q   K   A   V   E
        430                 450                 470
AGGAGGCTGGATGCAGAGGACCGGCCTGGAACAGTAAGCTGCAGTACATCCTGG
  E   E   L   D   A   E   D   R   P   A   W   N   S   K   L   Q   Y   I   L   A
        490                 510                 530
CCCAGATTGGCTTCTCTGTGGGCTTGGGCAACATCTGGAGGTTCCCTACCTGTGCCAGA
  Q   I   G   F   S   V   G   L   G   N   I   W   R   F   P   Y   L   C   Q   K
        550                 570                 590
AAAATGGAGGAGGTGCTTACCTGGTGCCTGTGCTGATCATCATCGGGATCC
  N   G   G   A   Y   L   V   P   Y   L   V   L   L   I   I   I   G   I   P
        610                 630                 650
```

MATCH WITH FIG. 1B

FIG. 1B

MATCH WITH FIG. 1A

CCCTCTTCTCCTGAGCTGGCTGTGGGTCAGAGGATCCGCCGGGAAGCATCGGTGTGT
 L  F  F  L  E  L  A  V  G  Q  R  I  R  R  G  S  I  G  V  W
670                        690                    710

GGCACTATATATGTCCCCGCCTGCTTCTCCAGTGCTGCATAGTCTGTCTCT
 H  Y  I  C  P  R  L  G  G  I  G  F  S  S  C  I  V  C  L  F
     730                        750                    770

TTGTGGGGCTGTATTATAATGTGATCATCGGGTGGAGCATCTTCTATTTCTTCAAGTCCT
 V  G  L  Y  Y  N  V  I  I  G  W  S  I  F  Y  F  F  K  S  F
     790                        810                    830

TCCAGTACCCGCTGCCCTGGAGTGAATGTCCTGTCGTCAGGAATGGGAGCGTCGCAGTGG
 Q  Y  P  L  P  W  S  E  C  P  V  V  R  N  G  S  A  V  V
     850                        870                    890

TGGAGGCAGAGTGTGAAAAGAGCTCAGCACTACTTCTGGTACCGAGAGGCTTTGG
 E  A  E  C  E  K  S  S  A  T  T  Y  F  W  Y  R  E  A  L  D
     910                        930                    950

ACATCTCTGACTCCATCTCGGAGAGTGGGCCCTCAACTGGAAGATGACCCTGTGCCTCC
 I  S  D  S  I  S  E  S  G  G  L  N  W  K  M  T  L  C  L  L
     970                        990                   1010

TCGTGGTCTGGAGCATCGGGGGATGGCTGTCGGTAAGGCATCCAGTCCTCGGGGAAGG
 V  V  W  S  I  G  G  M  A  V  G  K  G  I  Q  S  S  G  K  V
     1030                       1050                   1070

TGATGTATTTCAGCTCCTTCTTCCCCTGCCTGCTGTGCTTCCTGGTCCGGGGGT
 M  Y  F  S  S  L  F  P  Y  V  V  L  A  C  F  L  V  R  G  L
     1090                       1110                   1130

TGTTGTTGCGAGGGCAGTTGATGCATCCTACACATGTTCACTCCAAGCTGGTCAAGA
 L  R  G  A  V  D  G  I  L  H  M  F  T  P  K  L  V  K  M
     1150                       1170                   1190

TGCTGACCCCCAGTGTGGCGGGAGGTAGCTACCCAGGTCTTCTTTGGCTTGGGTCTGG
 L  D  P  Q  V  W  R  E  V  A  T  Q  V  F  F  G  L  G  L  G

MATCH WITH FIG. 1C

FIG. 1C

MATCH WITH FIG. 1B

```
                              1230                              1250
;CTTGGTGGTGTCATTGTCTTCTCCAGTTACAATAAGCAGGACAACTGCCACTTCG
 F  G  G  V  I  V  F  S  S  Y  N  K  Q  D  N  C  H  F  D
      1270                              1290                    1310
ATGGCGCCCCTGGTGTCCTTCATCAACTTCTTCACGTCAGTGTTGGCCACCCTCGTGGTGT
 G  A  L  V  S  F  I  N  F  F  T  S  V  L  A  T  L  V  V  F
      1330                              1350                    1370
TTGTTGTTTTGGGCTTCAAGGCCAACATCATGAATGAGAAGTGTGTGGTCGAGAATGCTG
 V  V  L  G  F  K  A  N  I  M  N  E  K  C  V  V  E  N  A  E
      1390                              1410                    1430
AGAAAATCCTAGGGTACCTTAACGTCCTGAGCCGGGACCTCATCCCCACCCCACG
 K  I  L  G  Y  L  N  T  N  V  L  S  R  D  L  I  P  P  H  V
      1450                              1470                    1490
TCAACTTCTCCCACCTGACCACAAAGGACTACATGGAGATGGACAATGTCATCATGACCG
 N  F  S  H  L  T  T  K  D  Y  M  E  M  D  N  V  I  M  T  V
      1510                              1530                    1550
TGAAGGAGGACCAGTTCTCAGCCCTGGGCCTTGACCCCTGCCTTCTGGAGGACGAGCTGG
 K  E  D  Q  F  S  A  L  G  L  D  P  C  L  L  E  D  E  L  D
      1570                              1590                    1610
ACAAGTCCGTGCAGGGCACAGGCCTGGCCTTCATCGCCTTCACTGAGGCCATGACGCACT
 K  S  V  Q  G  T  G  L  A  F  I  A  F  T  E  A  M  T  H  F
      1630                              1650                    1670
TCCCCACCTCCCCGTTCTGGTCCGTCATGTTCTTCTTGATGCTTATCAACCTGGGCCTGG
 P  T  S  P  F  W  S  V  M  F  F  L  M  L  I  N  L  G  L  G
      1690                              1710                    1730
GCAGCATGATCGGGACCATGGCAGGCATCACCACGCCCATCATCGACACCTCCAAGGTGC
 S  M  I  G  T  M  A  G  I  T  T  P  I  I  D  T  S  K  V  P
      1750                              1770                    1790
```

MATCH WITCH FIG. 1D

FIG. ID

MATCH WITH FIG. IC

```
CCAAGGAGATGTTCACAGTGGGCTGCTGTGTCTTACATTCCTGTGGGACTGTTGTTCG
 K  E  M  F  T  V  G  C  C  V  F  T  F  L  V  G  L  L  F  V
                           1810                          1850
TCCAGCGCTCCGGAAACTACTTTGTCACCATGTTCGATGACTACTCAGCCACGCTGCCAC
 Q  R  S  G  N  Y  F  V  T  M  F  D  D  Y  S  A  T  L  P  L
                           1870                          1910
TCACTCTCATCGTCATCCTTGAGAACATCGCTGTGGCCTGGATTTATGGACCCAAGAAGT
 T  L  I  V  I  L  E  N  I  A  V  A  W  I  Y  G  P  K  K  F
                           1930                          1970
TCATGCAGGAGCTGACGGAGATGCTGGGCTTCCGCCCCTACCGCTTCTATTTCTACATGT
 M  Q  E  L  T  E  M  L  G  F  R  P  Y  R  F  Y  F  Y  M  W
                           1990                          2030
GGAAGTTCGTGTCTCCACTATGCATGGCTGTGCTCACCACAGCCAGCATCATCCAGCTGG
 K  F  V  S  P  L  C  M  A  V  L  T  T  A  S  I  I  Q  L  G
                           2050                          2090
GGGTCACGCCCCCGGCCTACAGCGCCTGGATCAAGGAGGAGGCTGCCGAGCGCTACCTGT
 V  T  P  P  A  Y  S  A  W  I  K  E  E  A  A  E  R  Y  L  Y
                           2110                          2150
ATTTCCCCAACTGGCCCATGGCACTCCTGATCACCCTCATCGTCGTGGCGACGCTGCCCA
 F  P  N  W  P  M  A  L  L  I  T  L  I  V  V  A  T  L  P  I
                           2170                          2210
TCCCTGTGGTTCGTGTTCGTGCGGCACTTCCACTTGCTCTCTGATGGCTCCAACACCCTCT
 P  V  V  F  V  L  R  H  F  H  L  L  S  D  G  S  N  T  L  S
                           2230                          2270
CCGTGTCCTACAAGAAGCCCGCATGATGAAGGACATCTCCAACCTGGAGGAGAACGATG
```

MATCH WITH FIG. IE

MATCH WITH FIG. 1D

```
                 2290                           2310                            2330
AGACCCGGCTTCATCCTCAGCAAGGTGCCCAGTGAGGCACCTTCCCCCATGCCCACTCACC
 T  R   F  I  L   S  K  V   P  S  E   A  P   S  P  M   P  T   H  R
          2350                           2370                            2390
GTTCCTATCTGGGGCCCGGCAGCACATCACCCCTGGAGACCAGCTGGAACCCCAATGGAC
 S  Y   L  G  P   G  S  T   S  P  L   E  T   S  W  N   P  N   G  P
          2410                           2430                            2450
CCTATGGGCGCGGCTACCTGCTGGCCAGCACCCCTGAGTCTGAGTCTGTGACCACTGCCCA
 Y  G   R  G  Y   L  L  A   S  T  P   E  S   E  L   *
          2470
AGCCCATGCCCCGGCTCTCCCCCACCG
```

FIG. 1E

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 2485 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( x i ) SEQUENCE DESCRIPTION: SEQ ID NO:1:

```
CGGAGGCAGG GAGTGAGGAG CGAGCGGAGT CGCGTGCGCC GGCGCGAGCT CCGGGTCGCC    60
CCAGCCCCAG CCGGGGGCCT GTGGCGGGGG AGGAGCTGTG CGTCCGCGAC CCGTCGGGAT    120
CGCAGCTGCT CGGCCGGAGT GCACGGGCCG AGTCTGCGCG ACTACCCACG CGTGACAGGT    180
CCCTGAATGA GAAGGAGCTG ACAGCAGCTG AATTCCATCT TCTCTGTGTG CTGGGGAGCA    240
GGGCTACACG GCCCAGGTGG CATCAATGCC GAAGAACAGC AAAGTGACCC AGCGTGAGCA    300
CAGCAGTGAG CATGTCACTG AGTCCGTGGC CGACCTGCTG GCCCTCGAGG AGCCTGTGGA    360
CTATAAGCAG AGTGTACTGA ATGTGGCTGG TGAGGCAGGC GGCAAGCAGA AGGCGGTGGA    420
GGAGGAGCTG GATGCAGAGG ACCGGCCGGC CTGGAACAGT AAGCTGCAGT ACATCCTGGC    480
CCAGATTGGC TTCTCTGTGG GCCTCGGCAA CATCTGGAGG TTCCCCTACC TGTGCCAGAA    540
AAATGGAGGA GGTGCTTACC TGGTGCCCTA CCTGGTGCTG CTGATCATCA TCGGGATCCC    600
CCTCTTCTTC CTGGAGCTGG CTGTGGGTCA GAGGATCCGC CGCGGAAGCA TCGGTGTGTG    660
GCACTATATA TGTCCCCGCC TGGGGGGGAT CGGCTTCTCC AGCTGCATAG TCTGTCTCTT    720
TGTGGGGCTG TATTATAATG TGATCATCGG GTGGAGCATC TTCTATTTCT TCAAGTCCTT    780
CCAGTACCCG CTGCCCTGGA GTGAATGTCC TGTCGTCAGG AATGGGAGCG TCGCAGTGGT    840
GGAGGCAGAG TGTGAAAAGA GCTCAGCCAC TACCTACTTC TGGTACCGAG AGGCTTTGGA    900
CATCTCTGAC TCCATCTCGG AGAGTGGGGG CCTCAACTGG AAGATGACCC TGTGCCTCCT    960
CGTGGTCTGG AGCATCGGGG GGATGGCTGT CGGTAAGGGC ATCCAGTCCT CGGGGAAGGT    1020
GATGTATTTC AGCTCCCTCT TCCCCTACGT GGTGCTGGCC TGCTTCCTGG TCCGGGGGTT    1080
GTTGTTGCGA GGGGCAGTTG ATGGCATCCT ACACATGTTC ACTCCCAAGC TGGTCAAGAT    1140
GCTGGACCCC CAGGTGTGGC GGGAGGTAGC TACCCAGGTC TTCTTTGGCT TGGGTCTGGG    1200
CTTTGGTGGT GTCATTGTCT TCTCCAGTTA CAATAAGCAG GACAACAACT GCCACTTCGA    1260
TGGCGCCCTG GTGTCCTTCA TCAACTTCTT CACGTCAGTG TTGGCCACCC TCGTGGTGTT    1320
TGTTGTTTTG GGCTTCAAGG CCAACATCAT GAATGAGAAG TGTGTGGTCG AGAATGCTGA    1380
GAAAATCCTA GGGTACCTTA ACACCAACGT CCTGAGCCGG GACCTCATCC CACCCACGT    1440
CAACTTCTCC CACCTGACCA CAAAGGACTA CATGGAGATG GACAATGTCA TCATGACCGT    1500
GAAGGAGGAC CAGTTCTCAG CCCTGGGCCT TGACCCCTGC CTTCTGGAGG ACGAGCTGGA    1560
CAAGTCCGTG CAGGGCACAG GCCTGGCCTT CATCGCCTTC ACTGAGGCCA TGACGCACTT    1620
CCCCACCTCC CCGTTCTGGT CCGTCATGTT CTTCTTGATG CTTATCAACC TGGGCCTGGG    1680
CAGCATGATC GGGACCATGG CAGGCATCAC CACGCCCATC ATCGACACCT CCAAGGTGCC    1740
CAAGGAGATG TTCACAGTGG GCTGCTGTGT CTTTACATTC CTCGTGGGAC TGTTGTTCGT    1800
```

-continued

```
CCAGCGCTCC GGAAACTACT TTGTCACCAT GTTCGATGAC TACTCAGCCA CGCTGCCACT 1860
CACTCTCATC GTCATCCTTG AGAACATCGC TGTGGCCTGG ATTTATGGAC CCAAGAAGTT 1920
CATGCAGGAG CTGACGGAGA TGCTGGGCTT CCGCCCCTAC CGCTTCTATT CTACATGTG  1980
GAAGTTCGTG TCTCCACTAT GCATGGCTGT GCTCACCACA GCCAGCATCA TCCAGCTGGG 2040
GGTCACGCCC CCGGCCTACA GCGCCTGGAT CAAGGAGGAG GCTGCCGAGC GCTACCTGTA 2100
TTTCCCCAAC TGGCCCATGG CACTCCTGAT CACCCTCATC GTCGTGGCGA CGCTGCCCAT 2160
CCCTGTGGTG TTCGTCCTGC GGCACTTCCA CCTGCTCTCT GATGGCTCCA ACACCCTCTC 2220
CGTGTCCTAC AAGAAGGCCC GCATGATGAA GGACATCTCC AACCTGGAGG AGAACGATGA 2280
GACCCGCTTC ATCCTCAGCA AGGTGCCCAG TGAGGCACCT TCCCCATGC  CCACTCACCG 2340
TTCCTATCTG GGGCCCGGCA GCACATCACC CCTGGAGACC AGCTGGAACC CCAATGGACC 2400
CTATGGGCGC GGCTACCTGC TGGCCAGCAC CCCTGAGTCT GAGCTGTGAC CACTGCCCAA 2460
GCCCATGCCC GCTCTCCCCC CACCG                                       2485
```

( 2 ) INFORMATION FOR SEQ ID NO:2:

( i ) SEQUENCE CHARACTERISTICS:
        ( A ) LENGTH: 727 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:2:

```
Met Pro Lys Asn Ser Lys Val Thr Gln Arg Glu His Ser Ser Glu
                  5                  10                  15
His Val Thr Glu Ser Val Ala Asp Leu Leu Ala Leu Glu Glu Pro
                 20                  25                  30
Val Asp Tyr Lys Gln Ser Val Leu Asn Val Ala Gly Glu Ala Gly
                 35                  40                  45
Gly Lys Gln Lys Ala Val Glu Glu Glu Leu Asp Ala Glu Asp Arg
                 50                  55                  60
Pro Ala Trp Asn Ser Lys Leu Gln Tyr Ile Leu Ala Gln Ile Gly
                 65                  70                  75
Phe Ser Val Gly Leu Gly Asn Ile Trp Arg Phe Pro Tyr Leu Cys
                 80                  85                  90
Gln Lys Asn Gly Gly Gly Ala Tyr Lys Val Pro Tyr Leu Val Leu
                 95                 100                 105
Leu Ile Ile Ile Gly Ile Pro Leu Phe Phe Leu Glu Leu Ala Val
                110                 115                 120
Gly Gln Arg Ile Arg Arg Gly Ser Ile Gly Val Trp His Tyr Ile
                125                 130                 135
Cys Pro Arg Leu Gly Gly Ile Gly Phe Ser Ser Cys Ile Val Cys
                140                 145                 150
Leu Phe Val Gly Leu Tyr Tyr Asn Val Ile Ile Gly Trp Ser Ile
                155                 160                 165
Phe Tyr Phe Phe Lys Ser Phe Gln Tyr Pro Leu Pro Trp Ser Glu
                170                 175                 180
Cys Pro Val Val Arg Asn Glu Ser Val Ala Val Val Glu Ala Glu
                185                 190                 195
Cys Glu Lys Ser Ser Ala Thr Thr Tyr Phe Trp Tyr Arg Glu Ala
                200                 205                 210
Leu Asp Ile Ser Asp Ser Ile Ser Glu Ser Gly Gly Leu Asn Trp
```

-continued

|     |     |     | 215 |     |     |     | 220 |     |     |     | 225 |
|-----|-----|-----|-----|-----|-----|-----|-----|-----|-----|-----|-----|

Lys Met Thr Leu Cys Leu Leu Val Val Trp Ser Ile Gly Gly Met
                230                     235                     240

Ala Val Gly Lys Gly Ile Gln Ser Ser Gly Lys Val Met Tyr Phe
                245                     250                     255

Ser Ser Leu Phe Pro Tyr Val Val Leu Ala Cys Phe Leu Val Arg
                260                     265                     270

Gly Leu Leu Leu Arg Gly Ala Val Asp Gly Ile Leu His Met Phe
                275                     280                     285

Thr Pro Lys Leu Val Lys Met Leu Asp Pro Gln Val Trp Arg Glu
                290                     295                     300

Val Ala Thr Gln Val Phe Phe Gly Leu Gly Leu Gly Phe Gly Gly
                305                     310                     315

Val Ile Val Phe Ser Ser Tyr Asn Lys Gln Asp Asn Asn Cys His
                320                     325                     330

Phe Asp Gly Ala Leu Val Ser Phe Ile Asn Phe Phe Thr Ser Val
                335                     340                     345

Leu Ala Thr Leu Val Val Phe Val Val Leu Gly Phe Lys Ala Asn
                350                     355                     360

Ile Met Asn Glu Lys Cys Val Val Glu Asn Ala Glu Lys Ile Leu
                365                     370                     375

Gly Tyr Leu Asn Thr Asn Val Leu Ser Arg Asp Leu Ile Pro Pro
                380                     385                     390

His Val Asn Phe Ser His Leu Thr Thr Lys Asp Tyr Met Glu Met
                395                     400                     405

Asp Asn Val Ile Met Thr Val Lys Glu Asp Gln Phe Ser Ala Leu
                410                     415                     420

Gly Leu Asp Pro Cys Leu Leu Glu Asp Glu Leu Asp Lys Ser Val
                425                     430                     435

Gln Gly Thr Gly Leu Ala Phe Ile Ala Phe Thr Glu Ala Met Thr
                440                     445                     450

His Phe Pro Thr Ser Pro Phe Trp Ser Val Met Phe Phe Leu Met
                455                     460                     465

Leu Ile Asn Leu Gly Leu Gly Ser Met Ile Gly Thr Met Ala Gly
                470                     475                     480

Ile Thr Thr Pro Ile Ile Asp Thr Ser Lys Val Pro Lys Glu Met
                485                     490                     495

Phe Thr Val Gly Cys Cys Val Phe Thr Phe Leu Val Gly Leu Leu
                500                     505                     510

Phe Val Gln Arg Ser Gly Asn Tyr Phe Val Thr Met Phe Asp Asp
                515                     520                     525

Tyr Ser Ala Thr Leu Pro Leu Thr Leu Ile Val Ile Leu Glu Asn
                530                     535                     540

Ile Ala Val Ala Trp Ile Tyr Gly Pro Lys Lys Phe Met Gln Glu
                545                     550                     555

Leu Thr Glu Met Leu Gly Phe Arg Pro Tyr Arg Phe Tyr Phe Tyr
                560                     565                     570

Met Trp Lys Phe Val Ser Pro Leu Cys Met Ala Val Leu Thr Thr
                575                     580                     585

Ala Ser Ile Ile Gln Leu Gly Val Thr Pro Pro Ala Tyr Ser Ala
                590                     595                     600

Trp Ile Lys Glu Glu Ala Ala Glu Arg Tyr Leu Tyr Phe Pro Asn
                605                     610                     615

```
Trp Pro Met Ala Leu Leu Ile Thr Leu Ile Val Val Ala Thr Leu
                620                 625                 630

Pro Ile Pro Val Val Phe Val Leu Arg His Phe His Leu Leu Ser
                635                 640                 645

Asp Gly Ser Asn Thr Leu Ser Val Ser Tyr Lys Lys Ala Arg Met
                650                 655                 660

Met Lys Asp Ile Ser Asn Leu Glu Glu Asn Asp Glu Thr Arg Phe
                665                 670                 675

Ile Leu Ser Lys Val Pro Ser Glu Ala Pro Ser Pro Met Pro Thr
                680                 685                 690

His Arg Ser Tyr Leu Gly Pro Gly Ser Thr Ser Pro Leu Glu Thr
                695                 700                 705

Ser Trp Asn Pro Asn Gly Pro Tyr Gly Arg Gly Tyr Leu Leu Ala
                710                 715                 720

Ser Thr Pro Glu Ser Glu Leu
                725
```

( 2 ) INFORMATION FOR SEQ ID NO:3:

( i ) SEQUENCE CHARACTERISTICS:
        ( A ) LENGTH: 30 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:3:

GACTAAAGCT TGGCATCAAT GCCGAAGAAC                   30

( 2 ) INFORMATION FOR SEQ ID NO:4:

( i ) SEQUENCE CHARACTERISTICS:
        ( A ) LENGTH: 29 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:4:

GAACTTCTAG AGCAGTGGTC ACAGCTCAG                    29

( 2 ) INFORMATION FOR SEQ ID NO:5:

( i ) SEQUENCE CHARACTERISTICS:
        ( A ) LENGTH: 38 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:5:

GACTAAGATC TGCCACCATG CCGAAGAACA GCAAAGTG          38

( 2 ) INFORMATION FOR SEQ ID NO:6:

( i ) SEQUENCE CHARACTERISTICS:
        ( A ) LENGTH: 29 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:6:

GAACTGATAT CGCAGTGGTC ACAGCTCAG  29

NEUROTRANSMITTER TRANSPORTER

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a neurotransmitter transporter and the polypeptide of the present invention is herein sometime referred to as "NTT". The invention also relates to inhibiting the action of such polypeptides.

An essential property of synaptic transmission is the rapid termination of action following neurotransmitter release. For many neurotransmitters, including catecholamines, serotonin, and certain amino acids (e.g., γ-aminobutyric acid (GABA), glutamate, and glycine), rapid termination of synaptic action is achieved by the uptake of the transmitter into the presynaptic terminal and surrounding glial cells by neurotransmitter transporters (Bennett, et al., Life Sci. 15:1045–1056 (1974)). Inhibition or stimulation of neurotransmitter uptake provides a means for modulating the strength of the synaptic action by regulating the available levels of endogenous transmitters. Neurotransmitter transporters are membrane-bound polypeptides which uptake neurotransmitters into the pre-synaptic neuron after the neurotransmitters have crossed the synaptic cleft and acted upon the post-synaptic neuron. Neurotransmitters can be excitatory, such as glutamate, or inhibitory such as GABA.

Affinity neurotransmitter transport is thought to terminate the overall process of synaptic transmission (Iversen, L. L., Br. J. Pharmacol. 41:571–591 (1971)). Recently, cDNAs encoding more than ten different neurotransmitter transporters have been cloned and sequenced. The family of these genes could be divided into three subfamilies, including the GABA and taurine transporters (Liu, Q. R., et al., Proc. Natl. Acad. Sci. USA (in press), (1992)), the amino acid (glycine and proline) transporters (Fremeau, Jr., R. T., et al., Neuron, 8:915–926 (1992)), and the catecholamine transporters (Pacholczyk, T., et al., Nature, 350:350–354 (1991)). The general structure of all these gene products is very similar. They contain twelve potential transmembrane helices and an extended external loop with 3–4 glycosylation sites between membrane segments 3 and 4. The calculated molecular weights of the transporters is about 70 kDa and both their C- and N-terminal peripheral peptides contain about 40 amino acids and may be located on the cytoplasmic side of the membrane. In GABA and catecholamine transporter subfamilies, the amino acid sequence of each member is 60–80% identical to the other members within a subfamily and about 40% identical to members between the two subfamilies (Liu, Q. R., et al., Proc. Natl. Acad. Sci. USA, 89:6639–6643 (1992)). Amino acid transporters, such as the glycine transporter and proline transporter, share about 40–45% homology with all members of the neurotransmitter transporter superfamily. Sequence homology among the members of the neurotransmitter transporter family give clear indication that they evolved from a common ancestral gene. Moreover, partial genomic cloning of several neurotransmitter transporters reveal that in all of them the first intron in the reading frame is located in an identical position (id.).

A $GABA_A$ transporter was the first neurotransmitter system to be cloned and expressed (Guastella, J., et al., Science 249:1303–1306 (1990)) and is one of a family of neurotransmitter transporters cloned within the last year. Recently, a serotonin transporter cDNA has been disclosed in PCT WO 93/08261.

In accordance with one aspect of the present invention, there is provided a novel mature polypeptide which is herein referred to as NTT, as well as fragments, analogs and derivatives thereof. The polypeptide of the present invention is of human origin.

In accordance with another aspect of the present invention, there are provided polynucleotides (DNA or RNA) which encode such polypeptides.

In accordance with yet a further aspect of the present invention, there is provided a process for producing such polypeptide by recombinant techniques.

In accordance with yet a further aspect of the present invention, there are provided agonists which increase the affinity of NTT for its substrate, and which may be used to treat Amyotrophic Lateral Sclerosis, pain and stroke.

In accordance with a further aspect of the present invention, there are provided antibodies against such NTT polypeptides.

In accordance with yet another aspect of the present invention, there are provided antagonist/inhibitors which may be used to prevent the uptake of neurotransmitters by NTT, which may be used therapeutically, for example, in the treatment of depression, anxiety and epilepsy, as well as other neurologic or psychiatric disorders.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims. (FIGS. 1A, 1B, 1C, 1D and 1E collectively show (FIG. 1A illustrates the first portions of the polynucleotide sequence encoding the mature NTT polypeptide cDNA sequence (SEQ ID NO:1) and its corresponding amino acid sequence and FIGS. 1B–1E consecutively continue with the second, third, fourth and fifth parts, respectively, to the end of the same polynucleotide and amino acid sequences). The standard one-letter abbreviations are utilized to represent the amino acid residues in polypeptide sequence that is shown in FIGS. 1A–1E.

In accordance with an aspect of the present invention, there is provided an isolated nucleic acid (polynucleotide) which encodes for the mature polypeptide having the deduced amino acid sequence of FIG. 1A–1E or for the mature polypeptide encoded by the cDNA of the clone deposited as ATCC Deposit No. 75713 on Mar. 18, 1994. This deposit is a biological deposit with the ATCC, 12301 Parklawn Drive, Rockville, Md. 20852.

The polynucleotide of this invention was discovered in a cDNA library derived from a human fetal brain. It is structurally related to the neurotransmitter transporter family. It contains an open reading frame encoding a protein of about 727 amino acid residues. The protein exhibits the highest degree of homology to a rat neurotransmitter transporter (NT74) with 94% identity and 96% similarity over the entire amino acid sequence.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1A–1E or that of the deposited clone or may be a different coding sequence which coding sequence, as a result of the redundancy or degeneracy of the genetic code, encodes the same, mature polypeptide as the DNA of FIG. 1A–1E or the deposited cDNA.

The polynucleotide which encodes for the mature polypeptide of FIG. 1A–1E or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1A–1E or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1A–2E or the same mature polypeptide encoded by the cDNA of the deposited clone as well as variants of such polynucleotides which variants encode for a fragment, derivative or analog of the polypeptide of FIG. 1A–2E or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1A–1E or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of FIG. 1A–2E or the deposited cDNA.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to an NTT polypeptide which has the deduced amino acid sequence of FIG. 1A–1E or which has the amino acid sequence encoded by the deposited cDNA, as well as fragments, analogs and derivatives of such polypeptide.

The terms "fragment," "derivative" and "analog" when referring to the polypeptide of FIG. 1A–1E or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1A–1E or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the NTT genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.$ $coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker-genes to provide a phenotypic trait for selection of transformed host cells such as dihydrofolate reductase or neomycin resistance for eukaryotic cell culture, or such as tetracycline or ampicillin resistance in $E.$ $coli.$ The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E.$ $coli,$ Streptomyces, Salmonella typhimurium; fungal cells, such as yeast; insect cells such as Drosophila and Sf9; animal cells such as CHO, HEK 293, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by, for example, calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of $E.$ $coli$ and $S.$ $cerevisiae$ TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HEK 293, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The NTT polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The present invention also provides a method for identifying neurotransmitters which interact with the NTT polypeptides of the present invention. The method for determining whether a neurotransmitter is translocated from the synaptic cleft into the pre-synaptic neuron by NTT comprises transfecting a cell population with the appropriate vector expressing the NTT such that the cell will now express NTT. Various neurotransmitters are then radiolabelled, e.g., tritiated, and incubated with the transfected cell to identify which neurotransmitters are transported into the cell.

Once a neurotransmitter is identified compounds can be screened to identify those which specifically interact with NTT and either increase NTT's affinity to uptake its neurotransmitter, e.g., an agonist, or decrease its ability to uptake a neurotransmitter, e.g., an antagonist/inhibitor. This method comprises transforming host cells with a vector of the present invention such that the NTT polypeptide is expressed in that host, incubating the host cells with the natural neurotransmitter of NTT which has been labelled by a detectable marker sequence (e.g., radiolabel or a non-isotopic label such as biotin) and the potential compound and determining whether translocation of the neurotransmitter into the cell is either inhibited or increased. By measuring the amount of neurotransmitter inside the cell, one skilled in the art could determine if the compound is an effective agonist or antagonist.

The presence of excitatory or inhibitory neurotransmitters have important clinical significance. For example, glutamate is an excitatory neurotransmitter and its presence in the synaptic cleft can be toxic to neurons. This neuronal toxicity has been found to play a significant role in Amyotrophic Lateral Sclerosis or "ALS". Further, during a stroke excessive concentrations of glutamate are released into the synaptic cleft and are toxic to neuronal cells. Moreover, although the cause of general pain is unknown, it is believed that pain is characterized by the release of neurotransmitters into the synaptic cleft in the brain. Accordingly, an agonist of NTT may be employed to stimulate the uptake of neurotransmitters and therefore alleviate these above-mentioned conditions.

The NTT polypeptides of the present invention may be administered by expression of such polypeptides in vivo, which is often referred to as "gene therapy." Gene therapy is similar to the application of an NTT agonist, however, in gene therapy a polynucleotide of the present invention is administered such that the cellular machinery of the host expresses the NTT of the present invention to facilitate uptake of neurotransmitters where that is desired, for example in ALS, stroke and general pain.

For example, cells from a patient may be engineered with a polynucleotide (DNA or RNA) encoding a polypeptide ex vivo, with the engineered cells then being targeted to the neuronal cells of a patient where expression of NTT and translocation of neurotransmitters are desired. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

The present invention is also directed to antagonist/inhibitors of the polypeptides of the present invention, in addition to those identified by utilizing the above-described screening method. Antagonists include an antibody against the NTT polypeptide or, in some cases, an oligonucleotide which bind to the NTT making it inaccessible to its natural neurotransmitter allowing the concentration of the neurotransmitter in the synaptic cleft to increase.

Inhibitors include antisense constructs prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides of the present invention, is used to design an antisense RNA oligonucleotide of from about 10 to 40 base pairs in length. A DNA oligonucleotide is designed to be complementary to a region of the gene involved in transcription (triple helix -see Lee et al., Nucl. Acids Res., 6:3073 (1979); Cooney et al. Science, 241:456 (1988); and Dervan et al., Science, 251: 1360 (1991)), thereby preventing transcription and the production of NTT. The antisense RNA oligonucleotide hybridizes to the mRNA in vivo and blocks translation of the mRNA molecule into the NTT (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of NTT.

In these ways, the antagonist/inhibitors may be used to treat depression, anxiety, epilepsy and other neurological and psychiatric disorders. Defects in neurotransmitter transport systems result in increased or decreased concentrations of neurotransmitter in the synaptic cleft, resulting in improperly stimulated receptors. For example, it has been postulated that depression is associated with decreased release of norepinephrine and/or serotonin in the brain. Therefore, inhibiting NTT from translocating its neurotransmitter into the presynaptic neuron would allow these neurotransmitters to interact more frequently with their receptors. Accordingly, administration of the antagonist/inhibitors may be employed to alleviate the conditions mentioned above. The antagonist/inhibitors may be employed in a composition with a pharmaceutically acceptable carrier.

The present invention also relates to an assay for identifying potential antagonist/inhibitors specific to NTT. An example of such an assay comprises preparing a synaptosomal preparation from the hypothalamus of a mammal. Such a preparation is a "sealed" neuron where the end of the neuron is pinched off. The synaptosomal preparation is then incubated with tritiated neurotransmitter and a potential antagonist. The degree of uptake of neurotransmitter is then measured to determine if the antagonist is effective.

The compounds, e.g., agonist or antagonist/inhibitor compounds, of the present invention, may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The pharmaceutical compositions may be administered in an effective amount to effectively increase the affinity of NTT for its neurotransmitter or inhibit NTT from translocating its neurotransmitter, and thereby alleviate the abnormal conditions associated with excess concentrations of neurotransmitter in the synaptic cleft or concentrations of neurotransmitter which are too low, as the case may be.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clones to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clones from which the EST was derived, and the longer the better. For example, 2,000 bp is good, 4,000 is better, and more than 4,000 is probably not necessary to get good results a reasonable percentage of the time. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980). "Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of NTT

The DNA sequence encoding for NTT, ATCC # 75713 is initially amplified using PCR oligonucleotide primers corresponding to the 5' and sequences of the processed NTT protein (minus the signal peptide sequence) and the vector sequences 3' to the NTT gene. Additional nucleotides corresponding to NTT were added to the 5' and 3' sequences respectively. The 5' oligonucleotide primer has the sequence GACTAAAGCTTGGCATCAATGCCGAAGAAC (SEQ ID NO:3) contains a Hind III restriction enzyme site followed by 18 nucleotides of NTT coding sequence. The 3' sequence GAACTTCTAGAGCAGTGGTCACAGCTCAG (SEQ ID NO:4) contains complementary sequences to Xba I site and is followed by 18 nucleotides of NTT sequence. The restriction enzyme sites correspond to the restriction enzyme sites on the bacterial expression vector pQE-9. (Qiagen, Inc. 9259 Eton Avenue, Chatsworth, Calif., 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 was then digested with Hind III and Xba I. The amplified sequences were ligated into pQE-9 and were inserted in frame with the sequence encoding for the histidine tag and the RBS. The ligation mixture was then used to transform E. coli strain M15/rep 4 available from Qiagen under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized NTT was purified from this solution by chromatography on a Nickel-Chelate column under conditions that allow for tight binding by proteins containing the 6-His tag. Hochuli, E. et al., J. Chromatography 411:177-184 (1984). NTT was eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 2

Expression of Recombinant NTT in COS Cells

The expression of plasmid, NTT HA is derived from a vector pcDNAI/Amp (Invitrogen) containing: 1) SV40 origin of replication, 2) ampicillin resistance gene, 3) E. coli replication origin, 4) CMV promoter followed by a polylinker region, a SV40 intron and polyadenylation site. A DNA fragment encoding the entire NTT precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R.

Lerner, 1984, Cell 37, 767). The infusion of HA tag to our target protein allows easy detection of the recombinant protein with an antibody that recognizes the HA epitope.

The plasmid construction strategy is described as follows:

The DNA sequence encoding for NTT, ATCC # 75713, was constructed by PCR on the original EST cloned using two primers: the 5' primer GACTAAGATCTGCCACCAT-GCCGAAGAACAGCAAAGTG (SEQ ID NO:5) contains a Bgl II site followed by 21 nucleotides of NTT coding sequence starting from the initiation codon; the 3' sequence GAACTGATATCGCAGTGGTCACAGCTCAG (SEQ ID NO:6) contains complementary sequences to EcoR V site, translation stop codon, and the last 18 nucleotides of the NTT coding sequence. Therefore, the PCR product contains a Bgl II site, NTT coding sequence followed by a translation termination stop codon, and an EcoR V site. The. PCR amplified DNA fragment and the vector, pcDNAI/Amp, were digested with Bgl II and EcoR V. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant NTT, COS cells were transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the NTT HA protein was detected by radiolabelling and immunoprecipitation method. (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media were precipitated with a HA specific monoclonal antibody. Proteins precipitated were analyzed on 15% SDS-PAGE gels.

EXAMPLE 3

Expression Pattern of NTT in Human Tissue

Northern blot analysis was carried out to examine the levels of expression of NTT in human tissues. Total cellular RNA samples were isolated with RNAzol™ B system (Biotecx Laboratories, Inc. 6023 South Loop East, Houston, Tex. 77033). About 10 μg of total RNA isolated from each human tissue specified was separated on 1% agarose gel and blotted onto a nylon filter. (Sambrook, Fritsch, and Maniatis, Molecular Cloning, Cold Spring Harbor Press, (1989)). The labeling reaction was done according to the Stratagene Prime-It kit with 50 ng DNA fragment. The labeled DNA was purified with a Select-G-50 column. (5 Prime - 3 Prime, Inc. 5603 Arapahoe Road, Boulder, Colo. 80303). The filter was then hybridized with radioactive labeled full length MIP-2 gene at 1,000,000 cpm/ml in 0.5 M NaPO$_4$, pH 7.4 and 7% SDS overnight at 65° C. After wash twice at room temperature and twice at 60° C. with 0.5×SSC, 0.1% SDS, the filter was then exposed at −70° C. overnight with an intensifying screen. The message RNA for NTT is abundant in brain.

Numerous modifications and variations of the present invention are possible in light of the above teachings and, therefore, within the scope of the appended claims, the invention may be practiced otherwise than as particularly described.

What is claimed is:

1. An isolated polynucleotide comprising a polynucleotide having at least a 95% identity to a member selected from the group consisting of:
   (a) a polynucleotide encoding a polypeptide comprising amino acids 2 to 727 of SEQ ID NO:2; and
   (b) the complement of (a).

2. The isolated polynucleotide of claim 1 wherein said member is (a).

3. A recombinant vector comprising the polynucleotide of claim 2, wherein said polynucleotide is DNA.

4. A recombinant host cell comprising the polynucleotide of claim 2, wherein said polynucleotide is DNA.

5. The isolated polynucleotide of claim 1 wherein said member is (a) and said polypeptide comprises amino acids 1 to 727 of SEQ ID NO:2.

6. The isolated polynucleotide of claim 1, wherein the polynucleotide is DNA.

7. The isolated polynucleotide of claim 1, comprising a polynucleotide encoding a polypeptide comprising an amino acid sequence identical to amino acids 1 to 727 of SEQ ID NO:2.

8. The isolated polynucleotide of claim 1, wherein said polynucleotide is RNA.

9. A method of making a recombinant vector comprising inserting the isolated polynucleotide of claim 1 into a vector, wherein said polynucleotide is DNA.

10. The isolated polynucleotide of claim 1 comprising a polynucleotide comprising nucleotides 271 to 2450 of SEQ ID NO:1.

11. The isolated polynucleotide of claim 1 comprising the polynucleotide of SEQ ID NO:1.

12. An isolated polynucleotide comprising a polynucleotide having at least 95% identity to a member selected from the group consisting of:
   (a) a polynucleotide encoding the same polypeptide encoded by the human cDNA in ATCC Deposit No. 75713; and
   (b) the complement of (a).

13. The isolated polynucleotide of claim 12, wherein the member is (a).

14. The isolated polynucleotide of claim 12 wherein said polynucleotide comprises DNA identical to the coding portion of the human cDNA in ATCC Deposit No. 75713 which encodes a mature polypeptide.

* * * * *